(12) United States Patent
Caldwell

(10) Patent No.: US 7,436,986 B2
(45) Date of Patent: Oct. 14, 2008

(54) POSITIVE PATIENT IDENTIFICATION

(75) Inventor: Lloyd M. Caldwell, Salt Lake City, UT (US)

(73) Assignee: Bausch & Lomb Incorporated, Rochester, NY (US)

( * ) Notice: Subject to any disclaimer, the term of this patent is extended or adjusted under 35 U.S.C. 154(b) by 586 days.

(21) Appl. No.: 10/397,100

(22) Filed: Mar. 25, 2003

(65) Prior Publication Data

US 2004/0190759 A1 Sep. 30, 2004

(51) Int. Cl.
G06K 9/00 (2006.01)

(52) U.S. Cl. .................................... 382/117
(58) Field of Classification Search ............. None
See application file for complete search history.

(56) References Cited

U.S. PATENT DOCUMENTS

| | | | | |
|---|---|---|---|---|
| 4,109,237 | A * | 8/1978 | Hill | 382/117 |
| 4,641,349 | A | 2/1987 | Flom | 382/2 |
| 4,857,716 | A | 8/1989 | Gombrich | 235/462 |
| 5,572,596 | A | 11/1996 | Wildes | 382/117 |
| 5,751,836 | A | 5/1998 | Wildes | 382/117 |
| 5,901,238 | A | 5/1999 | Matsushita | 382/117 |
| 5,956,122 | A | 9/1999 | Doster | 351/210 |
| 5,991,730 | A | 11/1999 | Lubin | 705/3 |
| 6,119,096 | A | 9/2000 | Mann | 705/5 |
| 6,173,068 | B1 | 1/2001 | Prokoski | 382/115 |
| 6,247,813 | B1 | 6/2001 | Kim | 351/206 |
| 6,424,727 | B1 | 7/2002 | Musgrave | 382/117 |
| 6,505,193 | B1 | 1/2003 | Musgrave | 707/3 |
| 6,526,160 | B1 | 2/2003 | Ito | 382/117 |
| 2002/0150281 | A1 | 10/2002 | Cho | 382/117 |
| 2002/0154794 | A1 * | 10/2002 | Cho | 382/117 |

FOREIGN PATENT DOCUMENTS

| | | |
|---|---|---|
| CN | 1282048 A | 1/2001 |
| WO | WO 00/30525 | 6/2000 |

OTHER PUBLICATIONS

AC Williams, G.O. "Iris Recognition and Technology" IEEE Aerospace and Electronic systems Magazine, IEEE Inc. New York, US, vol. 12, No. 4, Apr. 1, 1997, p. 23-29, XP000677464.
U.S. Appl. No. 10/110,892 Entitled "Iris Recognition and Tracking for Treatment of Optical Irregularities of the Eye" filed Oct. 20, 2000, by Hohla, et al.
PCT Published Appln. No. WO 02/087442 Entitled "Iris Pattern Recognition and Alignment" published Nov. 7, 2002, by Youssefi, et al.

* cited by examiner

*Primary Examiner*—Matthew C Bella
*Assistant Examiner*—Alex Liew
(74) *Attorney, Agent, or Firm*—Jeffrey B. Powers

(57) ABSTRACT

A process and an enabling system and associated devices are directed to automatically and positively identifying a person based upon a matching comparison between a stored, historical iris recognition-based record and a contemporaneously obtained record. The algorithm involves identifying anchor features in selected regions of an iris image and mapping an iris pattern associated with the anchor features into a topologically consistent flat analysis space. Analysis according to the invention generates historical (reference) and contemporaneous Iris Feature Vectors for individuals upon which matching comparisons can be made to positively identify an individual from the reference base.

14 Claims, 4 Drawing Sheets

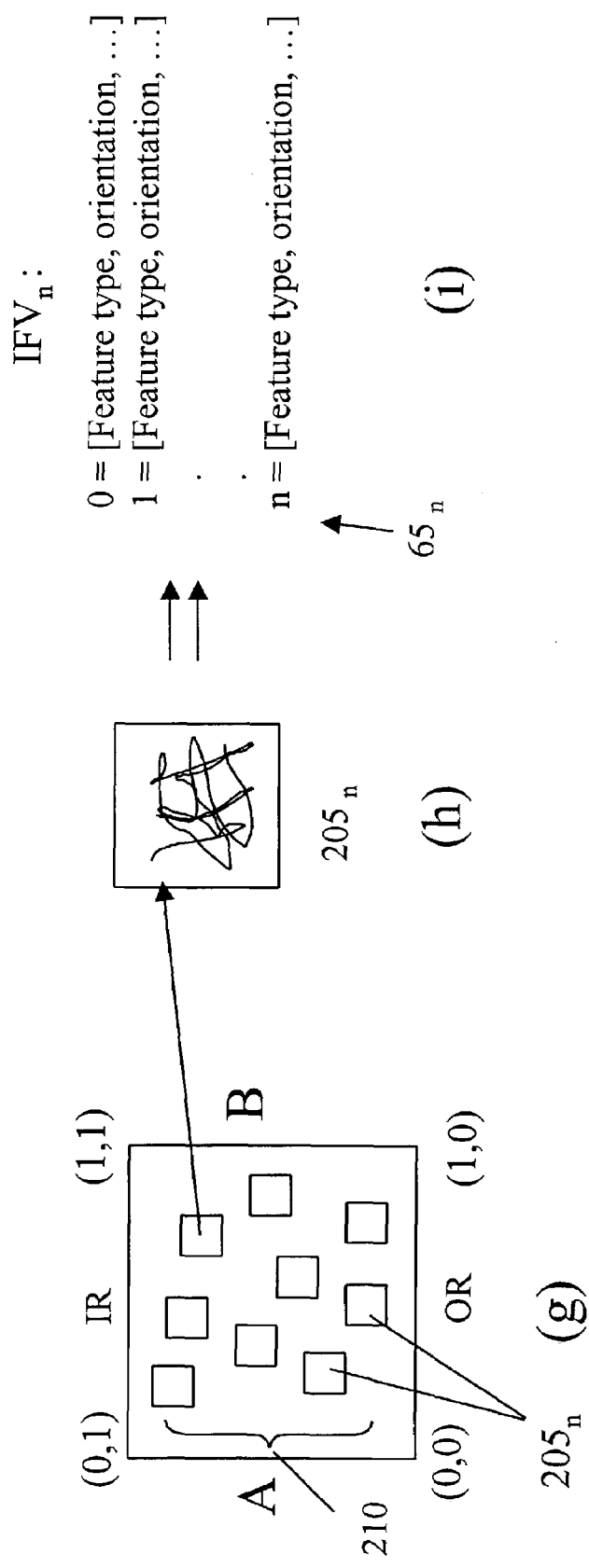
FIG. 2 (con't)

POSITIVE PATIENT IDENTIFICATION

BACKGROUND OF THE INVENTION

1. Field of the Invention

The invention is generally directed to an iris recognition identification method and associated devices and systems, and more particularly to positive patient identification especially directed to application in the field of vision correction, but in no way is it so limited.

2. Description of Related Art

The field of iris recognition has been home to many applications over the last 10 to 20 years. Interest in the development of iris recognition technology and methodologies can be attributed to the uniqueness of the iris pattern, akin to fingerprint individuality. Thus, iris pattern recognition as applied to personal identification and verification has spawned numerous inventions and abundant knowledge in the public domain, relating, for example, to security access, financial transactions, and patient identification, to name just a few.

The instant invention, while not limited in any way to the herein disclosed preferred embodiments, is directed to positive patient identification. A current practice for patient identification relies on an operator to enter patient data into manual and/or electronic record systems and generate a patient identifier. This patient identifier is then used to retrieve the patient record for subsequent diagnosis and treatment planning and execution. Errors in the entering or retrieval of patient records can lead to incorrect diagnoses and treatments having the potential for dire consequences.

In the field of vision correction, patient identification, screening, diagnostic, and/or treatment errors could result, for example, in the loss of vision rather than vision correction. Moreover, iris recognition applications relating to invasive eye procedures face unique challenges due to factors such as eye rotation between prone diagnostic positions and supine treatment positions, iris border recognition per se due to iris color variation among the general population, and difference between manifest and dilated states of the pupil.

In view of the above identified challenges and problems, and various technological shortcomings of the prior art, the inventor has recognized a need for a process and associated apparatus addressing these known issues, and for providing a positive patient identification method and system and associated advantages and benefits.

SUMMARY OF THE INVENTION

An embodiment of the invention is directed to a system for automatically, positively identifying a subject (person) based upon a matching comparison between a stored, historical iris recognition-based record and a contemporaneously obtained record. The system components include a light source for illuminating the subject's eye in order to generate identification data about the patient, a sensor that can detect the subject's eye data, and an optical system for relaying the subject's eye data to the sensor. Further included are means for capturing the data from the sensor, means for analyzing the captured data, and an information storage/retrieval component that includes a database of historical identification data for a plurality of subjects, means for obtaining a comparable contemporaneous identification data about a particular subject in the historical database, and means for comparing the contemporaneous identification data to the stored, historical data and determining a similarity relationship for the purpose of positively identifying the subject via a highly accurate match between the contemporaneous and historical information.

In all of the embodiments described herein, the subject(s) will be referred to as patients as the invention is particularly directed to the positive identification of patients in the field of vision correction. However, the scope of the invention is in no way limited to "patient" identification per se. This usage merely facilitates a more exemplary description of a preferred application in a field of practice.

In a preferred aspect of the foregoing embodiment, the eye illumination is in the near- to mid-infra-red which is used to reliably illuminate a wide and variable range in pupil contrast in a patient population. Preferred patient eye data includes an image of the patient's eye that is detected by a CCD sensor/camera assembly and transferred to an image data capture component which utilizes image processing and frame grabber technology. A suitably programmed computer such as, e.g., a PC can conveniently be used to analyze the captured data and to generate the historical and contemporaneous matching information that will be referred to hereinafter as contemporaneous and historical Iris Feature Vectors (IFVs). IFVs are generated for each patient from the obtained eye image. A patient database of historical (reference) IFVs is stored in an information storage/retrieval component of the system. The same (architecturally) system is utilized to obtain a contemporaneous IFV for a particular patient during a subsequent visit by the patient. The contemporaneous IFV can then be compared to the data set of stored, historical IFVs and a system computer component can determine a similarity relationship between the contemporaneous IFV and the set of historical IFVs to allow a positive identification of the patient.

A method embodiment of the invention is directed to obtaining the historical and/or contemporaneous IFVs as described above and facilitating a positive patient identification. The method includes the steps of acquiring an image of the patient's eye; determining inner and outer regions of the eye; defining search spaces within the inner and outer regions, respectively; and locating anchor features within each of the search spaces; determining an iris pattern and mapping this pattern into a normalized analysis space; sampling the analysis space via a pre-selected pattern of sampling regions; creating up to n preliminary IFVs for each sample region; generating an array of all preliminary IFVs, and storing the patient's historical IFV array in a storage/retrieval medium. Preferably, the stored array can be sorted based upon a gross and/or location invariant feature criteria. At some subsequent time, a contemporaneous IFV is generated for a particular patient and can be compared to the stored data set of historical IFVs for the entire patient population to make an automatic, positive identification of the patient.

A further embodiment of the invention is directed to a device-interpretable medium having encoded or stored therein a contemporaneous IFV as that term has been set forth above according to the invention.

In another embodiment, an ophthalmic diagnostic or therapeutic system is provided that can be instructed to carry out an algorithm for a positive patient identification, wherein the algorithm is represented by a process that generates and compares historical and contemporaneous IFVs as described herein according to the invention.

In summary, the process and apparatus embodiments of the invention are advantageous, in part, because they address the challenges in the field of application and problems in the prior art, rely on a patient inherent identifier not requiring a secondary record medium, utilize a feature that is unique to every individual, and can compensates for operator entered errors if they exist. These and other advantages and objects of the invention will become better apparent to the reader through the following detailed description, drawing figures, and appended claims.

DETAILED DESCRIPTION OF A PREFERRED EMBODIMENT OF THE INVENTION

Figure 1:
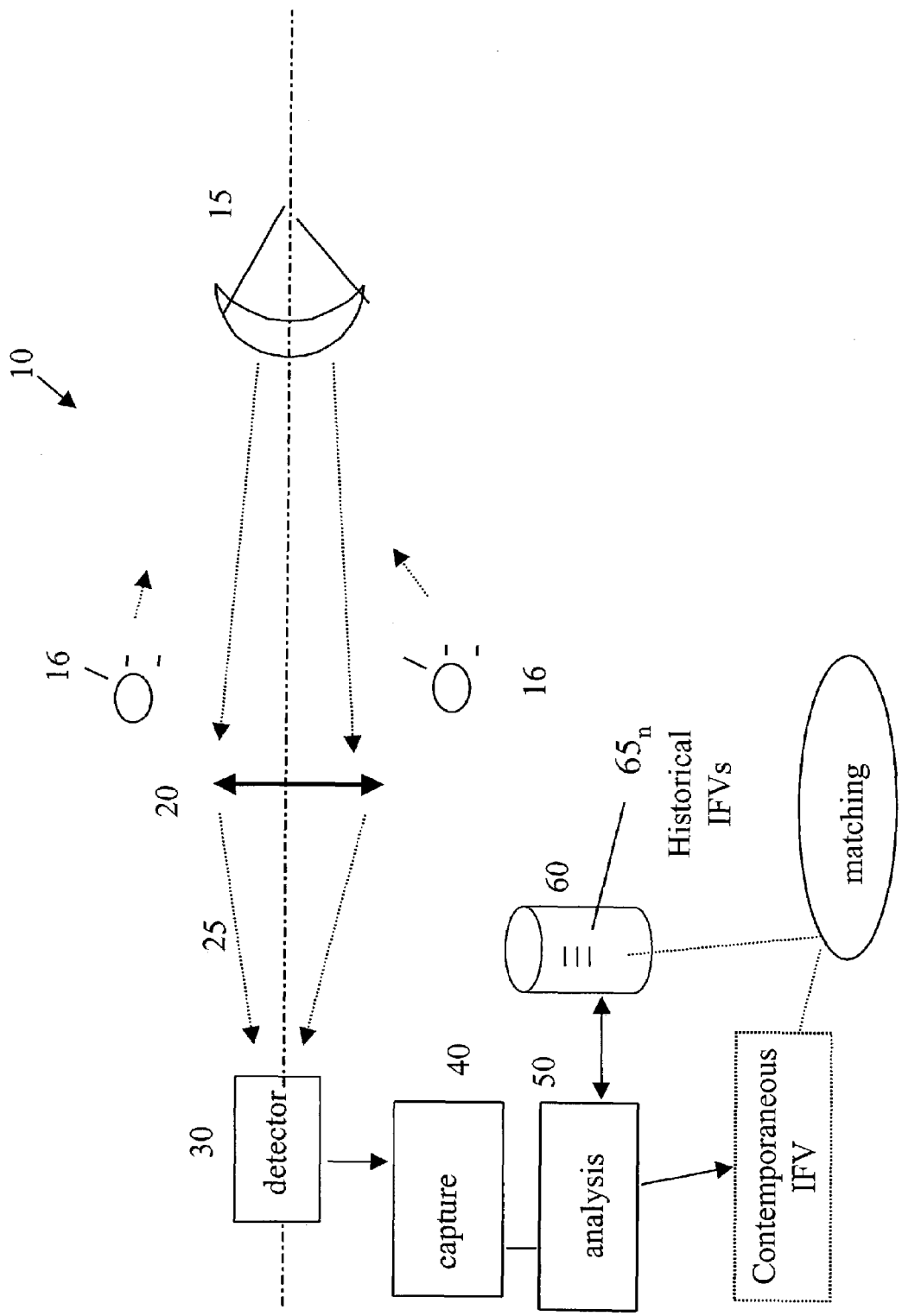
FIG. 1 is a diagrammatic illustration of a system embodiment according to the invention.

An embodiment of the invention is directed to a system 10 that provides for a positive patient identification as shown in FIG. 1. The system includes one or more eye illumination sources 16 that illuminate the patient's eye 15 in order to generate data 25 relating to patient identification. A properly aligned optical system 20 transfers the data to a detector/camera assembly 30. The detector/camera assembly is in operative engagement with image data capture means 40 for capturing the patient's eye data in suitable form from the detector/camera assembly. Analysis means 50 is operatively engaged with the capture means 40 and, based upon the patient eye data 25, generates an Iris Feature Vector (IFV) 65. At some initial time, an IFV 65 is generated for each patient in a patient population and stored in an information storage/retrieval component 60 that is in cooperative engagement with the analysis means 50. A database can then be assembled consisting of historical IFVs $65_n$ for the patient base. At some subsequent time when it is desired to identify a particular patient, a contemporaneous IFV 66 can be generated by the analysis means 50 and compared with the database of stored, historical IFVs to automatically, positively identify the patient. It may be desirable to include patient biographic information in the historical IFVs in addition to the data required by the algorithm according to the invention.

In a preferred aspect of the system 10, the illumination source(s) 16 emits light in the near- to mid-infrared spectrum between about 650 to 1000 nm, and more preferably between about 700 nm to 800 nm so as not to effect a pupil diameter change upon illumination. In addition, this wavelength range provides good illumination for iris imaging when other wavelength ranges might provide insufficient contrast for satisfactory iris imaging. The detector/camera 30 includes a CCD detector and camera for detecting and recording an iris image 25 via an optical system 20 well known in the art. Iris image data capture means 40 typically utilizes commercially available frame grabber/image processing hardware/software. The captured iris image information is processed as will be described in detail below, and is analyzed by analysis means 50, typically a PC or similar computer component. A database of historical IFVs $65_n$ are generated by the analysis means for the patient population and stored in a storage/retrieval component 60. The storage/retrieval component can be any of a variety of well known data storage/retrieval media located locally or remotely. For example, hard drives, portable memory media, servers, internet-based, and other storage/retrieval media are available. The analysis means 50 can also generate a contemporaneous IFV 66 for a particular patient that is used for comparison with the stored, historical IFVs. Based upon the indicia comprising the IFVs, typically only a single historical IFV will match any contemporaneous IFV, resulting in a positive patient identification.

Figure 2:
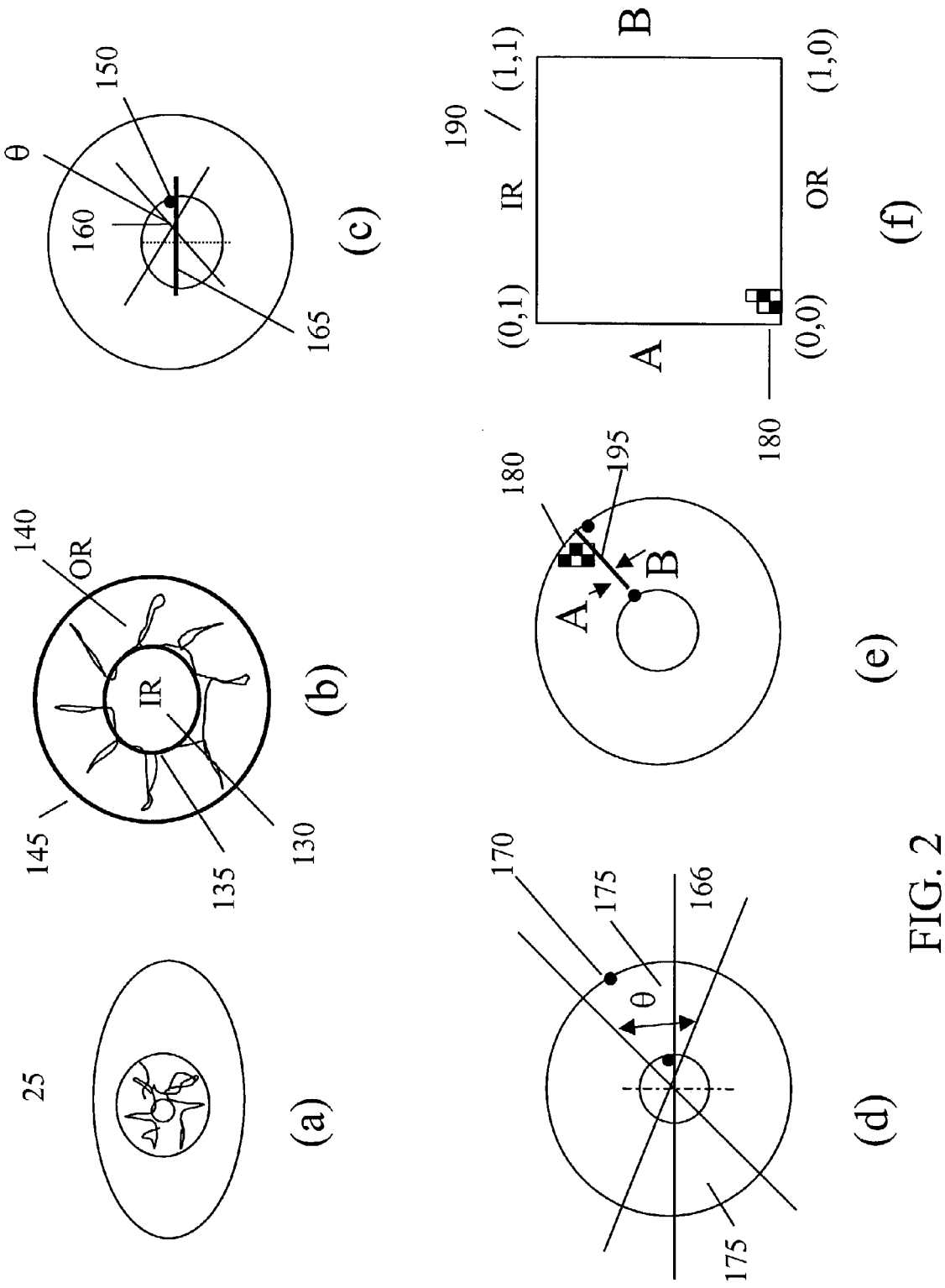
FIG. 2 is a diagrammatic illustration relating to a method embodiment according to the invention.
Figure 3:
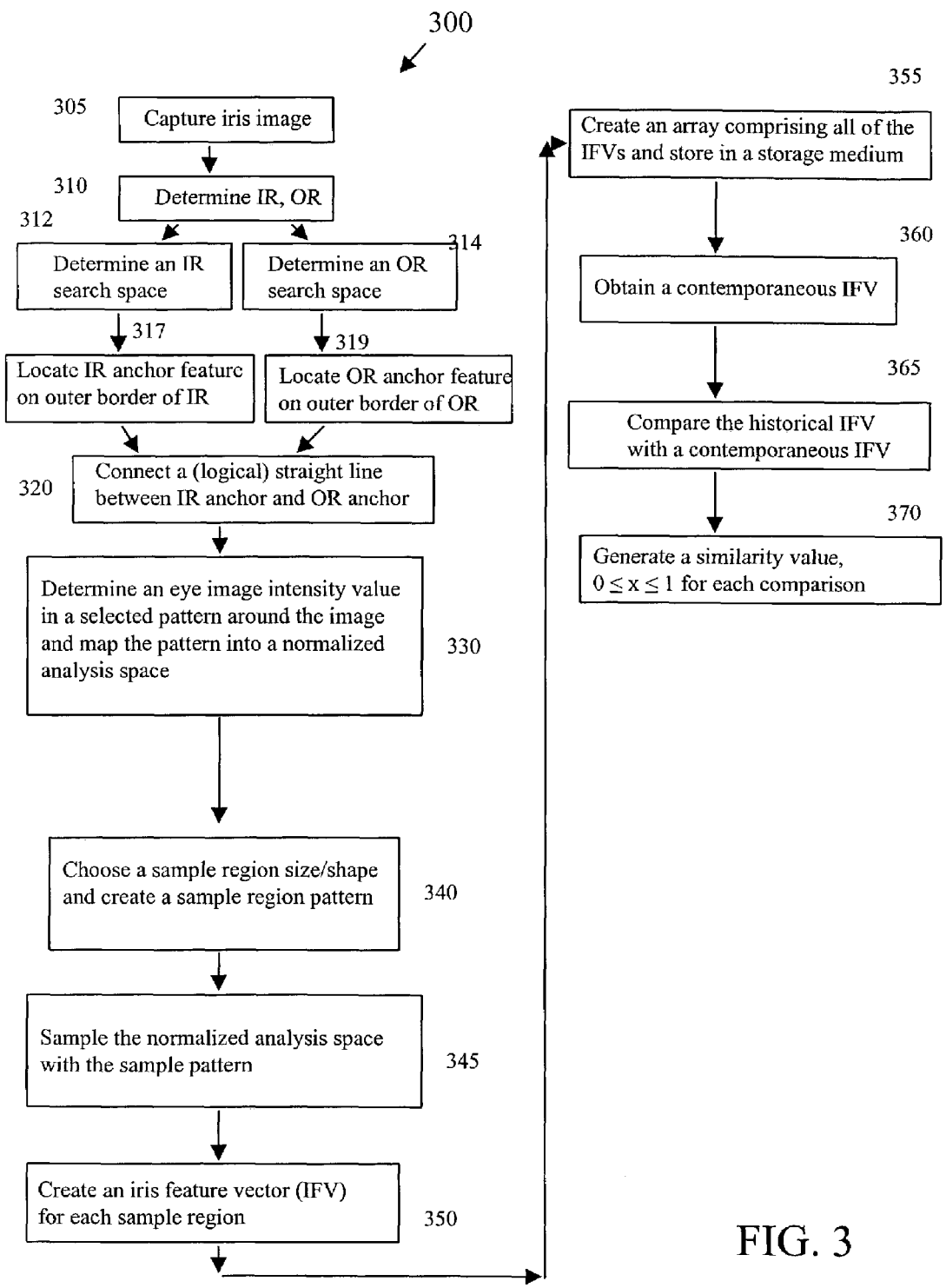
FIG. 3 is a flow chart type diagram setting forth the process steps of an algorithm embodiment according to the invention.

Another embodiment of the invention is directed to a method for positively identifying a patient. The method is based upon an algorithm 300 set forth in block diagram in FIG. 3 and described as follows with reference to FIG. 2. At step 305 an iris image 35 of the patient's eye is made and captured as represented in FIG. 2A. The iris image is processed to determine an inner region (IR) 130 and an immediately adjacent outer region (OR) 140 at step 310 and as shown in FIG. 2B. The inner region is delimited by a smooth outer boarder 135 that is a best-fit curve identifying the pupil/iris boundary of the patient's eye. Similarly, the outer region has an outer boundary 145 identified by a smooth, best-fit curve representing the limbus boundary of the patient's eye. The IR and OR boarder regions 135, 145 may be partially occluded due to eyelids, eyelashes, ambient illumination noise, etc., and, typically, the IR and OR will not be concentric as they may appear in FIG. 2B. An inner region search space 160 and an outer region search space 175 are then determined at steps 312, 314 as illustrated in FIGS. 2C and 2D. The inner region search space 160 is determined by constructing a horizontal line 165 that extends through the center of the inner region 130 to the IR border 135, and bounding the line 165 by an angular deviation, θ, of about ±10° from the horizontal. This IR search space represents approximately twice the maximum normal variability of eye rotation for a patient between a prone and a supine position. An outer region search space 175 is similarly determined by generating a horizontal line 166 through the center of the OR and bounding a space between the IR boundary 135 and the OR boundary 145 through an angle, θ, of about ±10° from the horizontal. At steps 317, 319 respectively, an inner region anchor feature 150 on the outer border 135 of the inner region, and an outer region anchor feature 170 on the outer border 145 of the outer region are located as shown in FIGS. 2C, 2D. Anchor features 150, 170 are preferably permanent landmarks of a particular patient's eye that are position invariant with respect to other changes in the eye, for example, dilated or manifest state. The anchor features are found using known filtering and thresholding techniques by searching the nasal and temporal regions bounded by the respective search spaces 160, 175. An example of an inner region anchor feature 150 is a region of maximum deviation from the IR border 135; however, other criteria can be used. For instance, uniform intensity regions of the iris which have no striations or fibrous artifacts, or non-uniform thickness regions exhibiting maximum/minimum thickness variations may be used for IR and/or OR anchor features. The outer region anchor feature 170 should be located using similar criteria as for the inner region anchor feature; i.e., the search space for this feature should, for example, be on the same side (nasal/temporal) as that identified in the inner region anchor feature detection. At step 320, a straight line (feature boarder) 195 is constructed connecting the IR anchor feature 150 and the OR anchor feature 170 as illustrated in FIG. 2E. The straight line 195 can be a logical straight line (i.e., formula generated) or otherwise generated (e.g., real) as one skilled in the art will understand. At step 330, an iris image pattern 180 is mapped into a normalized analysis space 190 illustrated in FIGS. 2E, 2F. The iris pattern 180 is determined by sampling image intensity (pixel) values in the region bounded by the IR, the OR, and the feature boarder 195. For example, sampling may take place by a precession around the iris image at a chosen angular and radial increment, or by horizontal and vertical increment sampling, or other methods. In particular, the sampling should be one-to-one in the mathematical sense and at a resolution sufficient for subsequent feature analysis. The detected intensity values (shown as black/white squares) are then mapped into a square grid 190 between the ranges 0,0 and 1,0 as illustrated in FIG. 2F. This provides a topologically consistent mapping between the iris image 25 and the normalized analysis space. Such normalization of the iris image removes any dependency upon the dilated or manifest pupil states, reduces or removes eye rotational contributions for prone/supine patient orientation, and creates a uniform invariant analysis space that simplifies subsequent processing. The next step in the analysis process involves a sample region selection as set forth at step 340 and illustrated with respect to FIG. 2G. A sample region pattern 210 is constructed by choosing the number, size, shape, and location of individual sample region boxes 205 as shown in FIG. 2G. It will be appreciated that the sample region boxes 205 need not be limited to square shapes as shown but, rather, can be any suitable shape/size/location. There is a tradeoff between IFV generation speed, match confidence values, sample region size and sample region quantity. For example; for a fixed number of sample regions, a larger region size will slow the IFV generation. For a fixed sample region size, a higher sample region quantity will slow the IFV generation. In all cases more sample regions yield higher match confidence values. Satisfactory results have been obtained when 20-30 sample boxes each having an area of approximately 1/25 of the total analysis region have been selected for the sample region pattern 210. Pattern 210 shape (i.e., box location) can be heuristically determined to minimize sample region selection in areas frequently occluded during image capture. Once the sample box 205 parameters and sample region pattern 210 are determined, this pattern will typically be used for all subsequent analysis, but is not limited in that manner by the invention. The normalized analysis space 190 is then sampled with the sample pattern at step 345. For each sampled region $205_n$ as shown in FIG. 2H, a preliminary $IFV_n$ is created at step 350. Once the normalized analysis space is sampled with the sample region pattern 210, a set of n iris feature vectors 65 for a particular patient is created as illustrated in FIG. 2I. The contents of each $IFV_n$ can be any combination of uniquely identifying characteristics; for example, each $IFV_n$ may consist of a feature-type (i.e., line, circle, ellipse, conic section, etc.), its major/minor axis of orientation, its maximum and minimum intensity, etc. Each $IFV_n$ may also contain information relating to the size, number, and location of the sample region boxes $205_n$, as well as operator entered patient data, or any other information that the operator wishes to be part of the patient's personal identification record. It is preferable that the feature-type component of each of the IFVs have a characteristic that allows each of the IFVs to sorted by a criteria that represents an invariant feature or a gross feature of the patient's eye. At step 355 each $IFV_n$ set 65 is assembled into an array and stored in a storage/retrieval medium such as that represented by 60 in FIG. 1. Each of these IFV arrays becomes an historical IFV for a patient, and historical IFVs $65_n$ for an entire patient population can be stored for later retrieval.

At some subsequent time, a need will arise to identify a particular patient. Accordingly, at step 360, all of the foregoing method steps are repeated to generate a contemporaneous IFV 66 of the particular patient. The contemporaneous IFV is a vector array similar to the historical IFV arrays that can be compared to the data set of stored historical IFVs and matched to one of them to positively identify the patient. The comparison of the contemporaneous and historical IFVs is performed at step 365 preferably by first comparing the location of the inner region/outer region border feature geometry or some other invariant feature supported by the sort criteria mentioned above. Then, at step 370, a similarity value, x, is generated between the values of 0 and 1 for each comparison of the contemporaneous IFV with the historical IFVs. The similarity value may be a root mean square calculation or other statistical evaluation as well understood in the art. Other similarity quantifiers may include (but are not limited to) counts of feature types in the IFV, median feature angle values, intensity variation, intensity variation rates, etc. . . . In the event that equivalent similarity values are generated for two matching records, it may become necessary to perturb the sample region box locations to break ties. The perturbation may be accomplished by shifting the sample region box locations or changing the sample region box size. The choice of which method to use may be based upon a priori knowledge of changes in the acquisition environment or random but small permutations of the sample region configuration.

In a related embodiment according to the invention, a storage/retrieval medium 60 has stored therein a plurality of historical IFVs obtained in accordance with the algorithm 300 described hereinabove. It will be understood that the medium for storing the historical IFVs is not limited to a particular hardware device or software architecture; rather, it may be internet-based, part of a local area network, regional server, local memory associated with a PC, or others.

In a further embodiment according to the invention, an ophthalmic diagnostic or therapeutic system 10 is provided that is capable of performing an algorithm 300 and of being programmed in such a manner to execute the algorithm for a positive patient identification according to the algorithm described hereinabove.

For each of the embodiments described herein, the contemporaneous IFV 66 may be generated and directly transmitted to the analysis means 50 or stored on any type of read/write medium that can be utilized by the system to make the comparison between the contemporaneous IFV and the stored, historical IFVs for positive patient identification. This read/write medium could, for example, take the form of a CD, DVD, floppy disc, encoded carrier wave, data transmission line, etc.

Notwithstanding the preferred embodiments specifically illustrated and described herein, it will be appreciated that various modifications and variations of the instant invention are possible in light of the description set forth above and the appended claims, without departing from the spirit and scope of the invention.

I claim:

1. A system for positively identifying a patient, comprising:

an eye illumination source;

a sensor configured to capture an image of the patient's eye containing an iris;

an optical system for transferring the image to the sensor;

means for analyzing the image;

an information storage/retrieval component coupled to the analyzing means and having stored therein a plurality of historical Iris Feature Vectors (IFVs) representing identification indicia of a plurality of patients;

wherein the analyzing means is adapted to generate from the image a contemporaneous IFV representing an identification indicia of the patient;

wherein the analyzing means is suitably programmed for comparing the contemporaneous IFV to the plurality of stored, historical IFVs, and determining a similarity relationship between the contemporaneous IFV and the historical IFVs, and wherein the analyzing means is adapted to identify in the image an inner region and an outer region, an inner region anchor feature located on an outer border of the inner region, and an outer region anchor feature located on an outer border of the outer region, the contemporaneous IFV being located in an analysis space bounded by the outer border of the inner region, and the outer border of the outer region and a third border extending between the inner region anchor feature and the outer region anchor feature, wherein said anchor features are landmarks of the patient's eye.

the outer border of the inner region being located at a pupil/iris boundary, and the outer border of the outer region being located at a limbus boundary.

2. A method for facilitating positively identifying a patient, comprising the following steps:
   a) acquire an image of the patient's eye containing an iris;
   b) determine an inner region and an outer region of the eye;
   c) locate an inner region anchor feature within a search space on an outer border of the inner region and located at a pupil/iris boundary;
   d) locate an outer region anchor feature within a search space on an outer border of the outer region and located at a limbus boundary;
   e) identify a third border extending between the inner region anchor feature and the outer region anchor feature, wherein said anchor features are landmarks of the patient's eye;
   f) determine a plurality of iris image intensity values in a region of the image bounded by the third border and the outer border of the inner region and the outer border of the outer region;
   g) map the intensity values into a normalized analysis space;
   h) create a pattern of sample regions, choosing a size and shape for each sample region;
   i) sample the normalized analysis space with the sample region pattern;
   j) create from 1 to n Iris Feature Vectors (IFVs) for each sample region;
   k) create an array of IFVs for the sample regions, and;
   l) store the array in a storage/retrieval medium.

3. The method of claim 2, wherein the array of stored IFVs comprise an historical IFV representing a particular patient's identification data set.

4. The method of claim 2 further comprising sorting the array of IFVs.

5. The method of claim 3, further comprising performing steps a) through k) at a subsequent time on a particular patient, wherein the subsequently obtained array comprises a contemporaneous IFV for the particular patient.

6. The method of claim 5, comprising comparing the contemporaneous IFV with a stored plurality of historical IFVs, and generating a similarity index, x, for each comparison, so as to match the contemporaneous IFV with an historical IFV.

7. The method of claim 6, wherein $0 \leq x \leq 1$.

8. The method of claim 6, comprising perturbing a sample region location in the sample region pattern when the similarity index is not sufficient to positively match the contemporaneous IFV with a single historical IFV.

9. A storage/retrieval medium having stored therein an historical IFV obtained in accordance with the method of claim 2.

10. A device readable medium having stored therein a contemporaneous IFV obtained in accordance with the method of claim 4.

11. An ophthalmic diagnostic or therapeutic system being sufficient to perform an algorithm, and being programmed in such a manner to execute the algorithm for a positive patient identification, said algorithm comprising:
   a) acquire an iris image of a patient's eye containing an iris;
   b) determine an inner region and an outer region of the eye;
   c) locate an inner region anchor feature within a search space on an outer border of the inner region and located at a pupil/iris boundary;
   d) locate an outer region anchor feature within a search space on an outer border of the outer region and located at a limbus boundary;
   e) identify a third border extending between the inner region anchor feature and the outer region anchor feature, wherein said anchor features are landmarks of the patient's eye;
   f) determine a plurality of iris image intensity values in a region of the image bounded by the third border and the outer border of the inner region and the outer border of the outer region into a normalized analysis space;
   g) map the intensity values into a normalized analysis space;
   h) create a pattern of sample regions, choosing a size and shape for each sample region;
   i) sample the normalized analysis space with the sample region pattern;
   j) create from 1 to n Iris Feature Vectors (IFVs) for each sample region;
   k) create an array of the IFVs, and;
   l) store the array in a storage/retrieval medium.

12. The system of claim 1, wherein the analyzing means is adapted to identify the contemporaneous IFVs within a sample regions inside the analysis space, the total area of the sample regions being less than the area of the analysis space.

13. The system of claim 12, wherein the sample region comprises a plurality of sample region boxes.

14. The system of claim 1, wherein the border extending between the inner region anchor feature and the outer region anchor feature is a straight line.

* * * * *